United States Patent
Dupelle et al.

(10) Patent No.: US 7,027,877 B2
(45) Date of Patent: Apr. 11, 2006

(54) METHOD OF APPLYING DEFIBRILATOR ELECTRODE PAD WITH FOLDED RELEASE SHEET

(75) Inventors: Michael R. Dupelle, Attleboro, MA (US); Deborah T. Jones, Dartmouth, MA (US)

(73) Assignee: ZOLL Medical Corporation, Burlington, MA (US)

( * ) Notice: Subject to any disclaimer, the term of this patent is extended or adjusted under 35 U.S.C. 154(b) by 0 days.

(21) Appl. No.: 09/938,063

(22) Filed: Aug. 23, 2001

(65) Prior Publication Data

US 2003/0040788 A1    Feb. 27, 2003

(51) Int. Cl.
*A61N 1/18* (2006.01)

(52) U.S. Cl. .................. 607/142; 607/152; 600/393

(58) Field of Classification Search .............. 602/57; 600/372, 382, 386, 391, 392; 607/115, 142, 607/11, 9, 152, 153
See application file for complete search history.

(56) References Cited

U.S. PATENT DOCUMENTS

| | | | |
|---|---|---|---|
| 2,897,961 A | 8/1959 | Bush | 206/63.2 |
| 3,085,577 A | 4/1963 | Berman et al. | 128/418 |
| 3,774,592 A | 11/1973 | Lahr | 128/2.1 E |
| 4,524,087 A | 6/1985 | Engel | 427/2 |
| 4,643,193 A | 2/1987 | DeMarzo | 128/639 |
| 5,150,708 A | 9/1992 | Brooks | 128/419 |
| 5,276,079 A | 1/1994 | Duan et al. | 524/386 |
| 5,571,165 A * | 11/1996 | Ferrari | 607/142 |
| 5,713,842 A * | 2/1998 | Kay | 602/57 |
| 5,846,217 A | 12/1998 | Beck et al. | 604/20 |
| 6,115,638 A | 9/2000 | Groenke | 607/142 |
| 6,140,549 A | 10/2000 | Pompei, Jr. | 602/57 |
| 6,178,357 B1 * | 1/2001 | Gliner et al. | 607/142 |
| 6,272,385 B1 * | 8/2001 | Bishay et al. | 607/142 |

FOREIGN PATENT DOCUMENTS

EP    0434258    * 12/1990

* cited by examiner

Primary Examiner—Robert E. Pezzuto
Assistant Examiner—Kristen Mullen
(74) Attorney, Agent, or Firm—Fish & Richardson P.C.

(57) ABSTRACT

A defibrillator electrode pad assembly has an adhesive release sheet configured to be removed while the electrode pad is held in a desired position on the patient. The release sheet is folded in a substantially U-shaped configuration and includes a pull-tab to be grasped by the user. The electrode pad is applied to the patient by positioning the electrode pad on the patient's skin with the release sheet facing the skin and in contact with or closely adjacent to the skin, without lifting the electrode pad from the patient's skin, pulling on the pull-tab to remove the release sheet to expose the adhesive portion, and adhering the adhesive portion to the patient's skin.

6 Claims, 5 Drawing Sheets

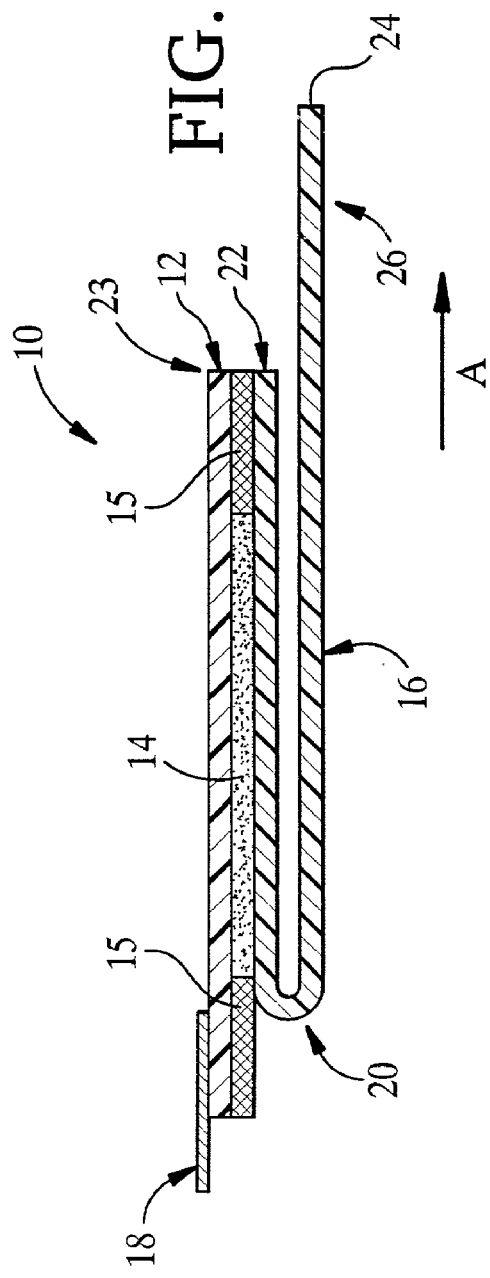
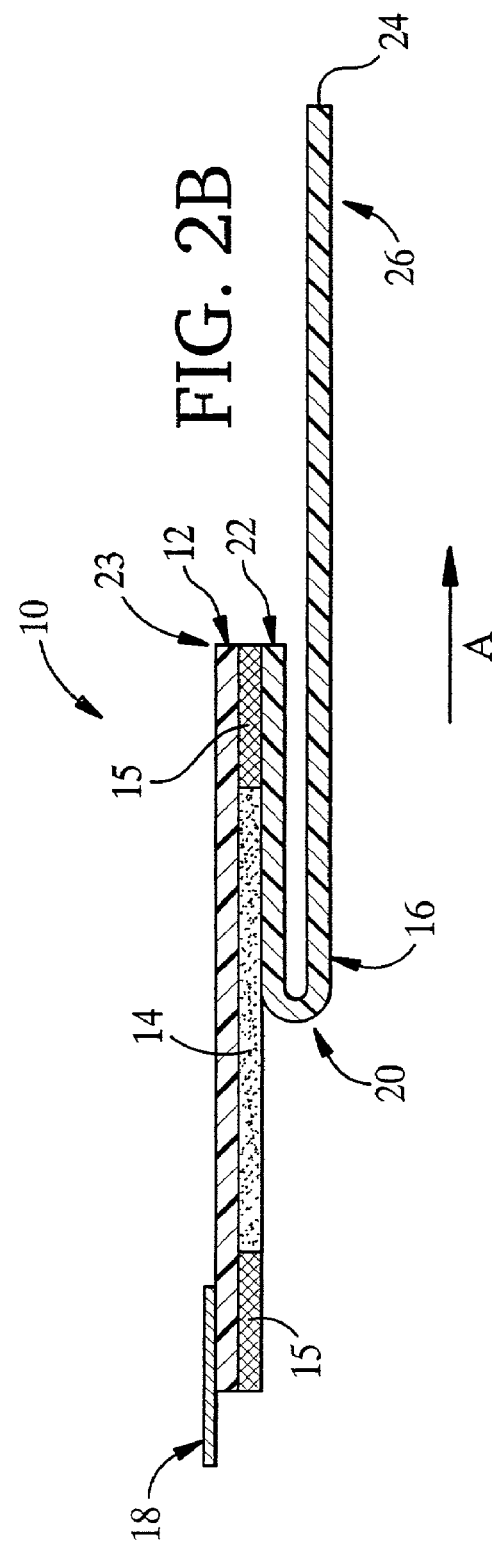

METHOD OF APPLYING DEFIBRILATOR ELECTRODE PAD WITH FOLDED RELEASE SHEET

TECHNICAL FIELD

This invention relates to skin-applied electrode pads, e.g., for use with defibrillators.

BACKGROUND

Skin-applied electrode pads are well known for use in medical applications such as cardiac pacing, ECG monitoring, and defibrillation. Typically, these electrode pads are attached to a wire lead or cable that is attached at its opposite end to the connector of a medical device or medical device instrumentation. Electrode pads generally include an electrode, e.g., a conductor such as a thin layer of tin or another metal, resting on a foam backing. The electrode typically is covered with a conductive gel that contacts a patient's skin and electrically connects the electrode to the patient, and the electrode pad includes a ring of adhesive surrounding the conductive gel to adhere the electrode to the patient's skin.

For one or more reasons, e.g., to prevent the adhesive gel from drying out, to maintain the electrodes in a sanitary condition, and to cover the adhesive until a caregiver is ready to adhere the electrode to the patient, a release sheet, e.g., a plastic cover, is positioned over the adhesive and/or conductive gel of each electrode.

To use the electrode pads, a caregiver connects the wire leads to an appropriate medical device such as a defibrillator (if they are not pre-connected), removes the release sheets from the electrode pads, and applies the electrode pads to the patient. If the caregiver does not correctly position the electrode pads on the first try, it may be difficult to reposition the electrode pads if the adhesive has adhered to the patient's skin. If the caregiver is able to remove and reposition the electrodes, adhesion may not be as good as it would have been had the electrode pads not been previously adhered. Also, if the electrodes are large in size and flexible, some of the electrode's adhesive surfaces may inadvertently adhere to each other during handling of the (release sheetless) electrode requiring the clinician to separate the stuck together portions prior to application to the patient. This "untangling" of the electrode can be frustrating, time consuming, difficult and may degrade the electrode's ability to adhere to the patient.

SUMMARY

Generally, the invention features an electrode pad in which an adhesive area is covered by a release sheet that is configured to be removed while the release sheet is in contact with or closely adjacent to a patient's skin. This arrangement allows the caregiver to carefully position the electrode pad with the release sheet in place, and then remove the release sheet without moving the electrode pad.

Because the release sheet can be removed from the electrode pad after the electrode pad has been properly positioned, without moving the electrode pad, accurate and precise placement can be achieved. Moreover, the need to remove, reposition and attempt to re-adhere an electrode pad that has already adhered to a patient's skin is eliminated and the likelihood that the electrode's adhesive surfaces will stick together during application is reduced. The time saved can literally be the difference between life and death in an emergency situation. For example, when defibrillation is required, every second of delay in applying the electrode pads can be critical.

In one aspect, the invention features a generally planar skin-applied electrode pad including: (a) an electrode, (b) an adhesive configured to adhere the electrode to a patient's skin, and (c) a release sheet, a first portion of the release sheet covering the adhesive, and a second portion of the release sheet extending from the first portion and being folded so that the release sheet can be peeled away from the adhesive by pulling the second portion in a direction substantially parallel to the plane of the electrode pad.

Some implementations may include one or more of the following features. The electrode pad includes a conductive gel, and the conductive gel is covered by the release sheet. The adhesive is non-conductive. The adhesive surrounds the gel. The release sheet is folded in a substantially U-shaped configuration. An edge of the second portion of the release sheet extends beyond an adjacent edge of the electrode, providing a pull-tab that can be grasped during removal of the release sheet. The release sheet is selected from the group consisting of release-coated papers, plastic sheet materials and polymeric films. The electrode pad includes a cable constructed to connect the electrode pad to a defibrillator control box. The electrode pad is configured for use with an automatic external defibrillator (AED), or a manual or semi-automatic external defibrillator.

In another aspect, the invention features a skin-applied electrode pad having a release sheet that is configured to be removed while the electrode pad is held in a desired position on the patient with a portion of the release sheet in contact with the patient's skin.

The invention also features, in another aspect, a defibrillator including a skin-applied electrode pad of the invention.

Some implementations may include one or more of the following features. The defibrillator is an automatic external defibrillator. Two or more electrode pads are integrally connected, forming an electrode pad assembly. The release sheet is folded in a substantially U-shaped configuration. An edge of the second portion of the release sheet extends beyond an adjacent edge of the electrode, providing a pull-tab that can be grasped during removal of the release sheet.

In yet another aspect, the invention features a method of applying an electrode to a patient, the electrode including an adhesive portion covered by a release sheet. The method includes (a) positioning the electrode on the patient's skin with the release sheet facing the skin and in contact with or closely adjacent to the skin, (b) without lifting the electrode from the patient's skin, removing the release paper to expose the adhesive portion, and (c) adhering the adhesive portion to the patient's skin.

Other features and advantages of the invention will be apparent from the detailed description and drawings, and from the claims.

DESCRIPTION OF DRAWINGS

FIGS. 2A and 2B are similar cross-sectional views, illustrating removal of the release sheet.

DETAILED DESCRIPTION

Figure 1:
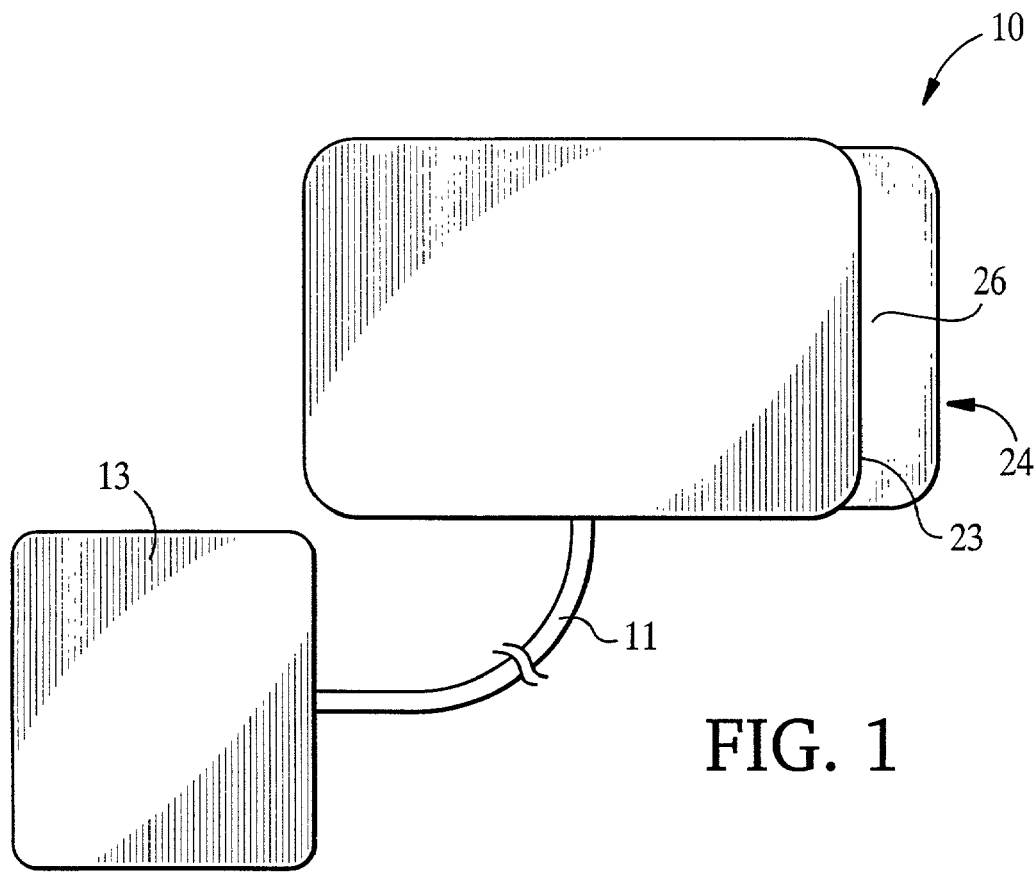
FIG. 1 is a top view of a prior art electrode pad.

An electrode pad 10 is shown in FIG. 1. When in use, electrode pad 10 is connected to a defibrillator control box 13 (not shown to scale) by cable 11.

Electrode pad 10 is relatively large, rendering it suitable for use in defibrillation. Typically, the surface area of electrode pad 10 is at least 50 $cm^2$, more preferably from about 50 $cm^2$ to 100 $cm^2$. Smaller medical electrodes, such as EKG electrodes, are generally much easier to place than the large defibrillator electrodes described above. This is in part due to the flexibility of the electrode, which makes the electrode difficult to control after the release paper is removed and can result in the sticking together problem discussed above in the Background.

Figure 2:
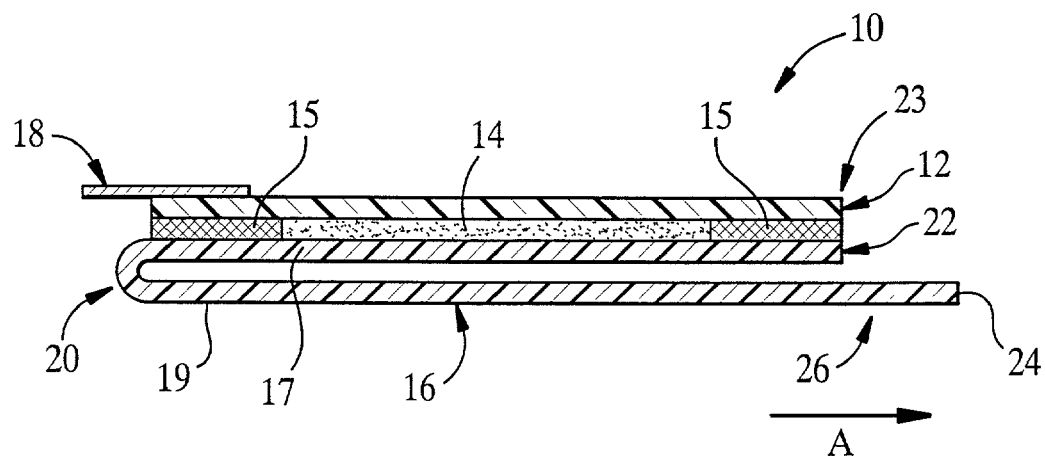
FIG. 2 is a cross-sectional view of an electrode pad according to one embodiment of the invention.

Referring to FIG. 2, electrode pad 10 includes an electrode 12, a conductive gel layer 14, an adhesive ring 15, and a release sheet 16. Optionally, electrode pad 10 may include a stabilizing tab 18 (not shown in FIG. 1), the function of which will be described below. Electrode 12 includes a foam backing or other suitable backing material (not shown), as is well known.

Figure 5:
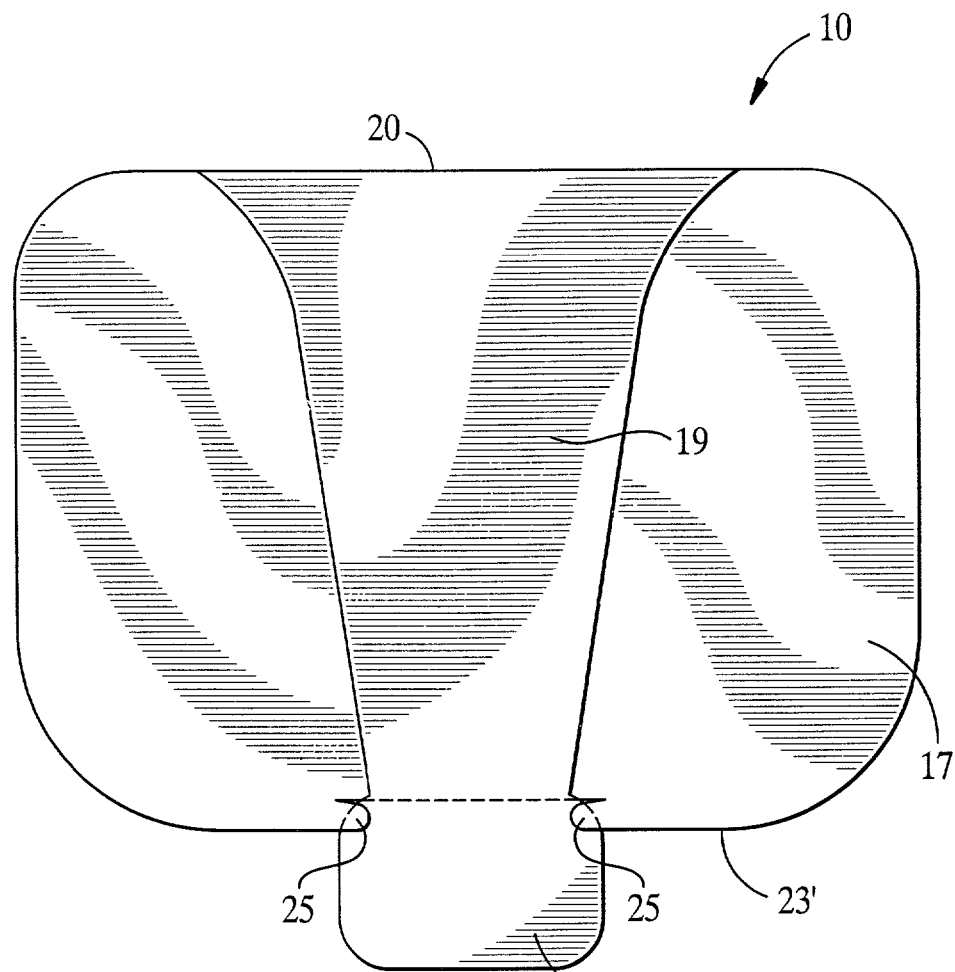
FIG. 5 is a back planar view of an electrode pad similar to that shown in FIG. 2.
Figure 5A:
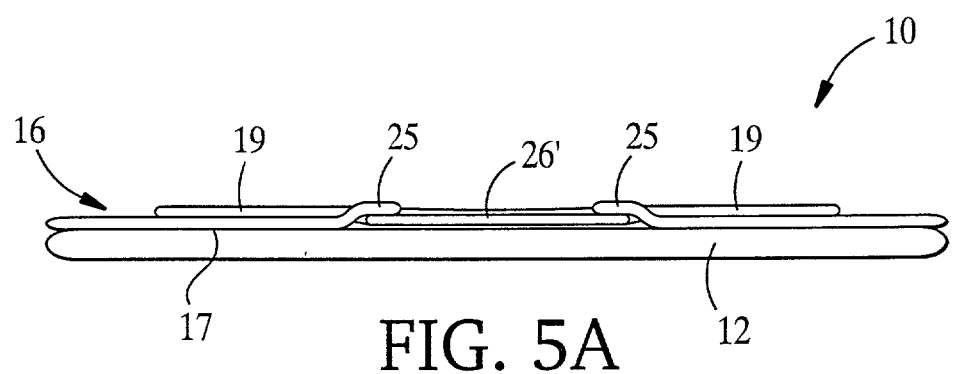

Release sheet 16 is folded, at fold 20, to define a generally U-shaped configuration, defining a portion 17 that is initially adhered to the adhesive and gel, and a portion 19 that extends freely beyond fold 20. The release sheet is folded in a manner so that it will not unfold to any significant extent during storage or prior to use. As shown in FIGS. 5 and 5A, the release sheet may also be held in place by a pair of tabs 25 extending from portion 17, under which pull tab 26 is disposed prior to use. Alternatively, a small area of pressure sensitive adhesive can be positioned in the same general area, on portion 17 or portion 19, to adhere the two portions together until use. Referring to FIG. 2, the end 22 of the release sheet that is adjacent the gel layer 14 is generally substantially aligned with the edge 23 of the electrode pad. The opposite end 24 of the release sheet extends beyond the edge 23 of the electrode pad, providing a pull-tab 26 which can be grasped by a user. Pull tab 26 preferably extends far enough beyond the edge 23 to provide a good grasp between the thumb and forefinger, typically at least about 1 inch.

To apply electrode pad 10 to a patient, a caregiver positions the electrode pad on the patient's chest in a desired position. When the caregiver is sure that the electrode pad is in the correct position, the caregiver holds the electrode pad in place, e.g., by grasping stabilizing tab 18, grasps pull tab 26, and peels the release sheet 16 out from underneath the electrode pad as indicated by arrow A in FIG. 2. Grasping stabilizing tab 18 while pulling on the pull tab 26 stabilizes the electrode and helps the caregiver to maintain the electrode in the desired position on the patient as the release sheet is removed. If stabilizing tab 18 is omitted, the same result may be obtained by lightly pressing the far side of the electrode (the side opposite the pull tab) against the patient while pulling the pull tab.

As the release sheet 16 is peeled off (FIGS. 2A and 2B), the fold 20 moves across the electrode pad in the direction of arrow A, so that the gel layer 14 is exposed and brought into contact with the patient's skin. As the gel layer and adhesive are exposed, the electrode pad adheres to the patient's skin and electrical contact is established. Light pressure may be applied to the electrode pad by the caregiver to ensure good adhesion.

The release sheet may be a release-coated paper, a plastic sheet material (including non-polymeric films having the properties of plastics), a polymeric film, or any other suitable sheet material having release properties sufficient to release from the gel layer and adhesive. Suitable sheet materials for use in the embodiment described above are also foldable. Examples of suitable sheet materials include polystyrene, polyester and paper.

Other embodiments are within the scope of the following claims. For example, the electrode pad may have any desired shape and size, including square, circular, or oval.

The adhesive ring may be formed of a non-conductive or conductive adhesive, and the adhesive may be provided in any other desired shape or configuration.

Figure 3:
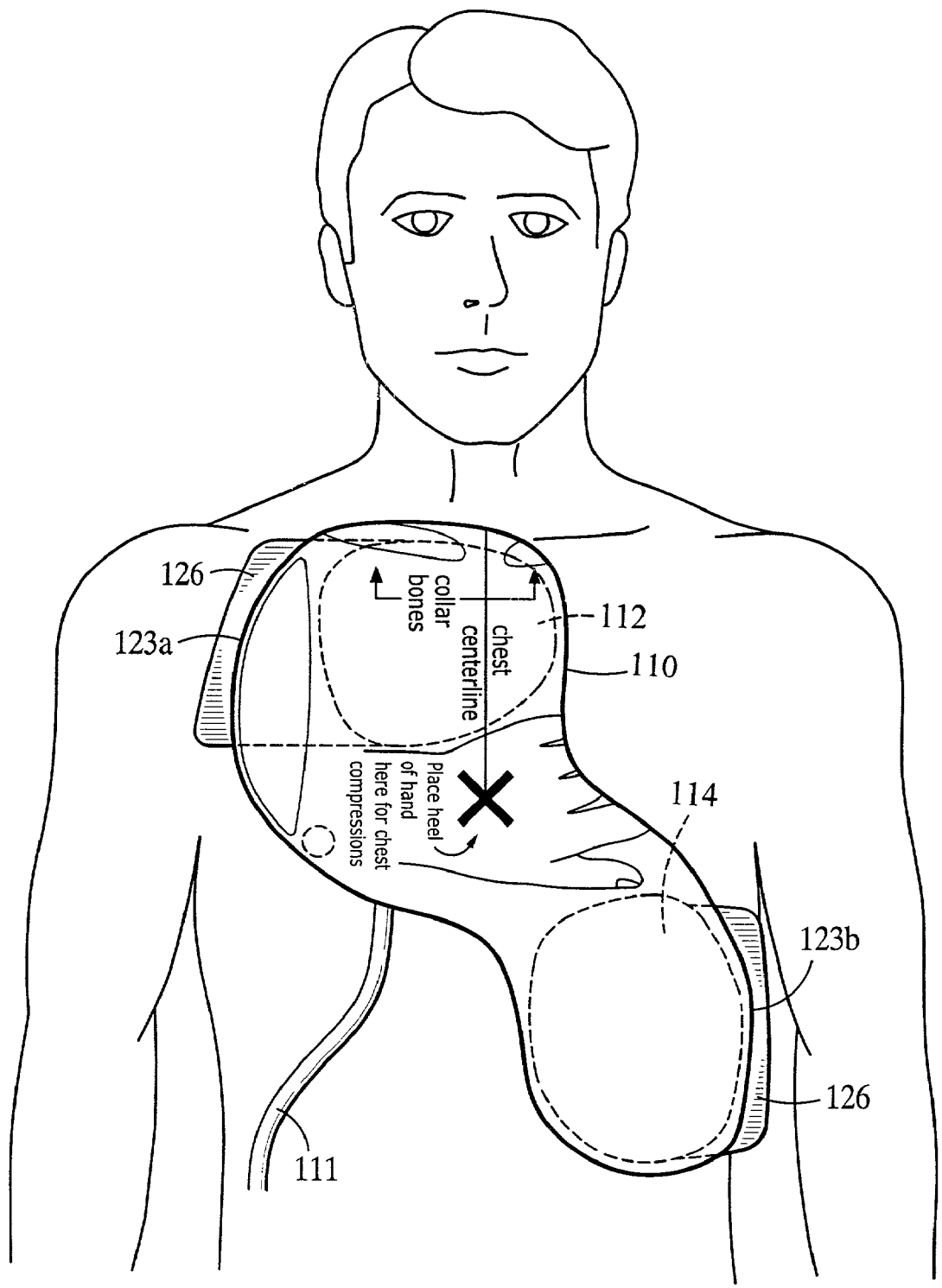
FIG. 3 is a drawing of an electrode pad assembly according to one embodiment of the invention, positioned over the chest of a patient.

The electrode pad may be integrally attached to one or more other electrode pads to form an electrode pad assembly, allowing a pair of electrodes to be easily applied to a patient, e.g., as disclosed in copending U.S. Ser. No. 09/794, 320, filed Feb. 27, 2001, the complete disclosure of which is incorporated herein by reference. Such an electrode pad assembly is shown in FIG. 3. Referring to FIG. 3, electrode pad assembly 110 includes a pair of electrode pads 112, 114. Electrode pad assembly 110 is connected by a cable 111 to a resuscitation control box (not shown). In this case, the pull-tabs 126 of the two electrode pads 112, 114 extend from opposite edges 123a, 123b of the electrode pad assembly so that they are exposed for use.

Moreover, the electrode pad or electrode pad assembly may include text or other indicia to help a caregiver locate the electrode, e.g., as disclosed in U.S. Ser. No. 09/794,320.

Figure 4:
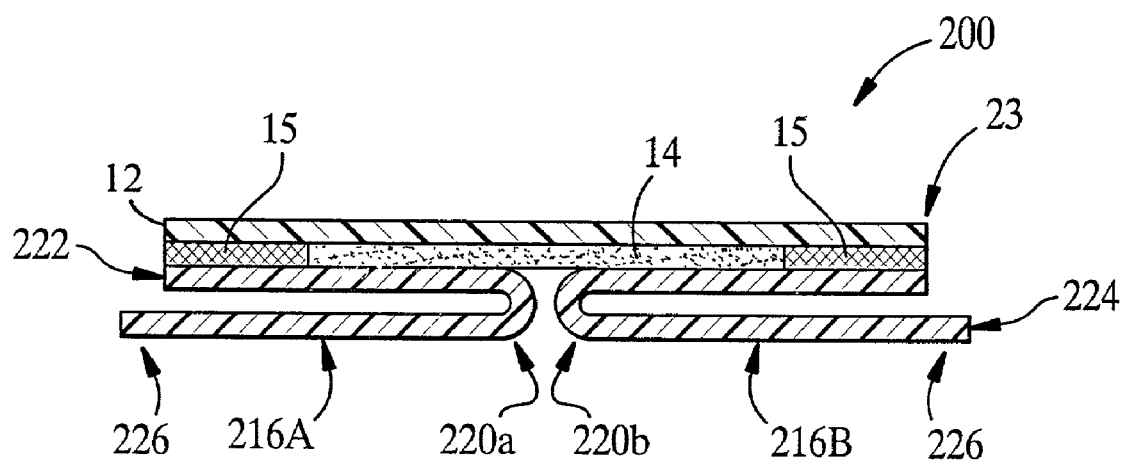
FIG. 4 is a cross-sectional view of an electrode pad according to an alternate embodiment of the invention.

In another embodiment, shown in FIG. 4, an electrode pad 200 includes a pair of U-folded release sheets 216a, 216b. Each release sheet is folded at a fold 220 (220a, 220b), to define a generally U-shaped configuration. The end 222 of each release sheet that is adjacent the gel layer 14 is generally substantially aligned with the edge 23 of the electrode pad. The opposite end 224 of each release sheet extends beyond the edge 23 of the electrode pad, providing a pull-tab 226 which can be grasped by a user. This option may be desirable when the electrode is circular or oval.

Portion 19 of the release sheet may be any desired shape. For example, portion 19 may be tapered as shown in FIG. 5. This taper facilitates removal of portion 19 and pull tab 26 from the tabs 25.

What is claimed is:

1. A method for applying a defibrillation electrode pad assembly to a patient, comprising removing an electrode pad assembly from a package, the electrode pad assembly comprising first and second electrodes, each of the electrodes sized and configured for external defibrillation, and each of the electrodes having a skin-contacting area of at least 50 centimeters squared;

a non-electrode area positioned between the first and second electrodes and mechanically connected to the first and second electrodes;

text or other indicia on the electrode pad assembly for helping a user position the electrodes in a desired position on the chest of a patient;

an electrical cable extending from the electrode pad assembly for connecting the electrodes to a defibrillator;

an adhesive area at each of the first and second electrode, the adhesive area configured to adhere an electrode to the skin of the patient, the adhesive area at the first electrode being separated from the adhesive area at the second electrode by an area without adhesive, and at least one release sheet covering each adhesive area, each release sheet being folded in a substantially U-shaped configuration, each release sheet having a tab sized and configured to be grasped by one hand of the user while the electrode pad assembly is positioned on the chest of the patient, and each release sheet being configured to be removed by the user pulling on the tab in a direction generally away from the non-electrode area, thereby causing the release sheet to peel away from the adhesive area, applying the electrode pad assembly to the patient by
positioning the first and second electrodes in the desired position on the chest,
holding the assembly in the desired position by applying pressure with one hand generally in the non-electrode area,
using another hand to pull on the tab of the release sheet at the first electrode, with the pulling being in a direction generally away from the non-electrode area, to thereby remove the release sheet from the first electrode,
repeating the process of holding the assembly in the desired position by applying pressure with one hand generally in the non-electrode area, and
using another hand to pull on the tab of the release sheet at the second electrode, with the pulling being in a direction generally away from the non-electrode area, to thereby remove the release sheet from the second electrode.

2. The method of claim 1 wherein the electrode pad assembly further comprises a conductive gel at the skin contacting area of each electrode.

3. The method of claim 2 wherein the adhesive area of each electrode comprises a non-conductive adhesive.

4. The method of claim 3 wherein the adhesive area surrounds the gel.

5. The method of claim 1 wherein the defibrillator electrodes are for connection to an automatic, semi-automatic or manual external defibrillator.

6. The method of claim 1 wherein the release sheets are configured so that, as the release sheets are peeled away, a fold about which the release sheet is folded travels in the direction in which the release sheet is pulled.

* * * * *